(12) United States Patent
Wu et al.

(10) Patent No.: US 11,752,161 B2
(45) Date of Patent: Sep. 12, 2023

(54) PHARMACEUTICAL COMPOSITIONS, METHOD OF MAKING AND METHOD OF USING THEREOF

(71) Applicant: Gannex Pharma Co., Ltd., Shanghai (CN)

(72) Inventors: Jinzi Jason Wu, Shanghai (CN); Xuyu Chai, Shanghai (CN)

(73) Assignee: GANNEX PHARMA CO., LTD., Shanghai (CN)

(*) Notice: Subject to any disclaimer, the term of this patent is extended or adjusted under 35 U.S.C. 154(b) by 108 days.

(21) Appl. No.: 17/212,623

(22) Filed: Mar. 25, 2021

(65) Prior Publication Data

US 2021/0308155 A1 Oct. 7, 2021

(30) Foreign Application Priority Data

Mar. 27, 2020 (CN) .......................... 202010227177.0

(51) Int. Cl.
*A61K 31/665* (2006.01)
*A61K 9/16* (2006.01)

(52) U.S. Cl.
CPC .......... *A61K 31/665* (2013.01); *A61K 9/1617* (2013.01); *A61K 9/1635* (2013.01); *A61K 9/1694* (2013.01)

(58) Field of Classification Search
CPC .. A61K 31/665; A61K 9/1617; A61K 9/1635; A61K 9/1694
See application file for complete search history.

(56) References Cited

U.S. PATENT DOCUMENTS

2009/0028925 A1  1/2009  Erion et al.

FOREIGN PATENT DOCUMENTS

| CN | 101180097 | 5/2008 | |
|---|---|---|---|
| CN | 113274368 | 8/2021 | |
| WO | 2005051298 | 6/2005 | |
| WO | 2005123729 | 12/2005 | |
| WO | 2006128055 | 11/2006 | |
| WO | 2006128058 | 11/2006 | |
| WO | 2011038207 | 3/2011 | |
| WO | 2017185083 | 10/2017 | |
| WO | 2017185087 | 10/2017 | |
| WO | 2018053036 | 3/2018 | |
| WO | 2018094265 | 5/2018 | |
| WO | 2018226604 | 12/2018 | |
| WO | WO 2018/226604 | * 12/2018 | ........... A61K 31/662 |
| WO | 2019183004 | 9/2019 | |
| WO | 2020117962 | 6/2020 | |
| WO | 2020117987 | 6/2020 | |

OTHER PUBLICATIONS

Huang et al., AAPS PharmSciTech, vol. 17, No. 1, Feb. 2016, pp. 106-119.*
Gupta et al., AAPS PharmSciTech, vol. 17, No. 1, Feb. 2016, pp. 148-157.*
Huang, S., O'Donnell, K.P., Keen, J.M. et al. A New Extrudable Form of Hypromellose: Affinisol™ HPMC HME. AAPS PharmSciTech 17, 106-119 (2016). https://doi.org/10.1208/s12249-015-0395-9.
Gupta, S.S., Solanki, N. & Serajuddin, A.T.M. Investigation of Thermal and Viscoelastic Properties of Polymers Relevant to Hot Melt Extrusion, IV: Affinisol™ HPMC HME Polymers. AAPS PharmSciTech 17, 148-157 (2016). https://doi.org/10.1208/s12249-015-0426-6.
Maddineni, S., Battu, S.K., Morott, J. et al. Influence of Process and Formulation Parameters on Dissolution and Stability Characteristics of Kollidon® VA 64 Hot-Melt Extrudates. AAPS PharmSciTech 16, 444-454 (2015). https://doi.org/10.1208/s12249-014-0226-4—Abstract.
M. Maniruzzaman et al., "Dissolution enhancement of poorly water-soluble APIs processed by hot-melt extrusion using hydrophilic polymers", Drug Development and Industrial Pharmacy,vol. 39, No. 2, Mar. 28, 2012 (Mar. 28, 2012), p. 218-227,—Abstract.
Anonymous, "Viking Therapeutics Announces Results of Gene Expression Analysis from In Vivo Study of VK2809 in Non-Alcoholic Steatohepatitis (NASH)", Sep. 11, 2017 (Sep. 11, 2017), Retrieved from the Internet: URL:http://ir.vikingtherapeutics.com/2017-09-11-Viking-Therapeutics-Announces-Results-of-Gene-Expression-Analysis-from-In-Vivo-Study-of-VK2809-in-Non-Alcoholic-Steatohepatitis-NASH.
International Search Report and Written Opinion, issued in International Patent Application No. PCT/CN2021/083207 dated Jun. 30, 2021.

* cited by examiner

*Primary Examiner* — Alicia L Otton
(74) *Attorney, Agent, or Firm* — Michael Ye; Rimon Law

(57) ABSTRACT

Pharmaceutical compositions suitable for long-term storage at room temperature are described. The pharmaceutical composition comprises the compound of formula (1)

(I)

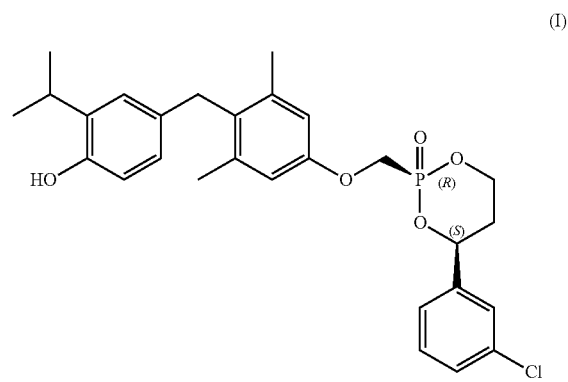

and can be used for the treatment of steatohepatitis. Also described are methods for preparing the pharmaceutical composition and methods of treatment using the pharmaceutical compositions.

13 Claims, 2 Drawing Sheets

PHARMACEUTICAL COMPOSITIONS, METHOD OF MAKING AND METHOD OF USING THEREOF

RELATED APPLICATIONS

This application claims priority of Chinese Application No. 2020102271770, filed on Mar. 27, 2020. The entirety of the aforementioned application is incorporated herein by reference.

FIELD

The invention belongs to the field of pharmaceutical preparations, and particularly relates to a cyclic phosphonate pharmaceutical composition suitable for storage at room temperature and a preparation method thereof.

BACKGROUND

The storage conditions of a drug product are a reflection of the stability of the drug in the drug product. Drugs or crystal forms with lower melting points are generally relatively less stable and need to be stored at lower temperatures, while drugs or crystal forms with higher melting points have better stability and can generally be stored at room temperature. The reasonable processing temperature of the preparation should also be reasonably determined according to the thermal stability of the drug. Thermal degradation of drugs is usually closely related to their melting point, and after 20° C. beyond the melting point, degradation reactions occur rapidly.

Steatohepatitis is a chronic inflammatory disease, thus long term medication is preferred. The requirement for low temperature storage will add many inconveniences to the long-term medication of patients, and may result missed administration or improper storage, which may affect the therapeutic effect, and may lead to delay or recurrent of the disease. In addition, the low-temperature refrigeration conditions also need to be equipped with special cold chain transportation vehicles and long-term use refrigerator, which bring additional costs to the commercial development of the product.

Therefore, in order to better meet clinical and commercial needs, it is necessary to find a stable pharmaceutical formulation and preparation method that enable the storage at room temperature. Such a formulation would not only greatly increase the in vivo and in vitro dissolution of the active ingredient, but more importantly, enable its storage at room temperature.

The compound shown in Formula (I) (Molecular formula C28H32C105P, Molecular weight 514.98, CAS No. 852948-13-1) is a novel oral thyroid hormone receptor-β (THR-β) agonist, which effectively promotes the decomposition of fatty acids and stimulates the biogenesis of mitochondria by selectively activating THR-β and regulating the expression of downstream genes such as CYP7A and SREBP-1c, reducing low-density lipoprotein and triglyceride levels, which in turn reduces lipotoxicity and improves liver function and reduces liver fat, and is a highly effective and low toxic candidate drug for nonalcoholic steatohepatitis.

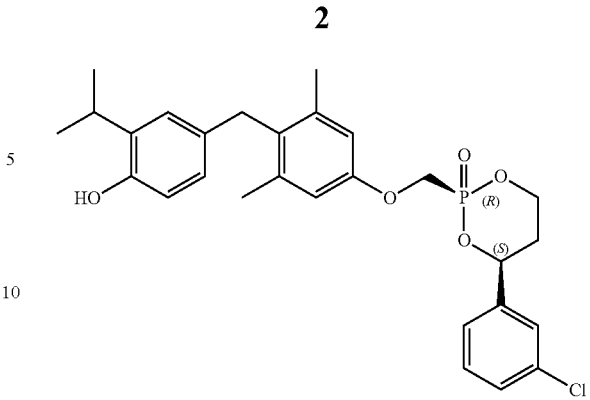

The compound shown in Formula (I) is a lipophilic insoluble drug, and its solubility in hydrochloric acid solution, buffer, and water without surfactant at 37° C. and pH 1.0~9.0 is less than 0.5 ng/mL. The very low solubility limits its use in the development as a drug candidate. Chinese patent application 202010105909.9 reports a semi-solid capsule technology that can substantially increase the dissolution of the compound shown in Formula (I), but the capsule needs to be stored in a cool place below room temperature, not exceeding 15° C., specifically in a closed container at 2 to 8° C.

Therefore, there still exist a need for developing formulations that would allow storage of pharmaceutical compositions comprising the compound of formula (I) at room temperature for an extended period of time.

SUMMARY

After extensive exploration and comparison of different kinds and ratios of excipients and process parameters, the inventors unexpectedly found that the high temperature hot melt extrusion process (greater than 80° C.) is suitable for the preparation of solubilized compositions of the compound of formula (I) and that products prepared with the formulations and methods described in the present application exhibit increased dissolution of the compound of formula (I), and long-term stability at room temperature, which is of great significance for improving compliance and safety of patients and also reducing transportation and storage costs.

One aspect of the present application relates to a pharmaceutical composition, comprising the following components in weight portions: (a) 1 part of the compound of formula and (b) 15 to 45 parts of copovidone with a glass transition temperature of 90° C. to 130° C., wherein components (a) and (b) are mixed and undergo hot melt extrusion.

Another aspect of the present application relates to a pharmaceutical composition, comprising the following components in weight portions: (a) 1 part of the compound shown in Formula (I) and (b) 6 to 20 parts of hydroxypropyl methylcellulose with a glass transition temperature of 90° C. to 130° C., wherein components (a) and (b) are mixed and undergo hot melt extrusion.

Another aspect of the present application relates to a method of preparing the pharmaceutical composition of the present application.

Another aspect of the present application relates to a method for treating steatohepatitis in a subject. The method comprises the step of administering to the subject an effective amount of the pharmaceutical composition of the present application.

Figure 1:
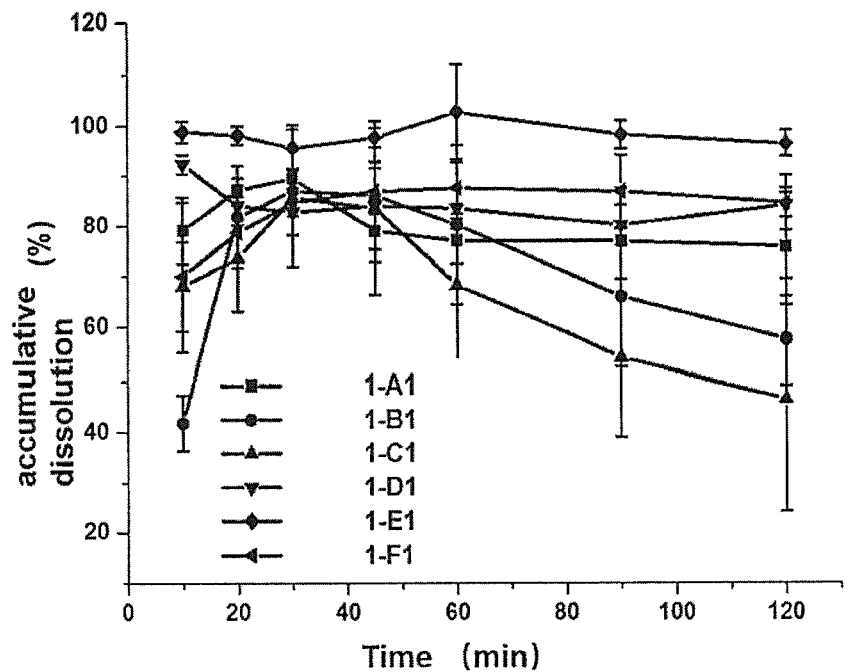
FIG. 1 is the dissolution curve (Effect Example 1) of the composition prepared according to A1-F1 formulation in Example 1 in water (n=6)

While the present disclosure will now be described in detail, and it is done so in connection with the illustrative embodiments, it is not limited by the particular embodiments illustrated in the figures and the appended claims.

DETAILED DESCRIPTION OF THE INVENTION

Reference will be made in detail to certain aspects and exemplary embodiments of the application, illustrating examples in the accompanying structures and figures. The aspects of the application will be described in conjunction with the exemplary embodiments, including methods, materials and examples, such description is non-limiting and the scope of the application is intended to encompass all equivalents, alternatives, and modifications, either generally known, or incorporated here. Unless otherwise defined, all technical and scientific terms used herein have the same meaning as commonly understood by one of ordinary skill in the art to which this application belongs. One of skill in the art will recognize many techniques and materials similar or equivalent to those described here, which could be used in the practice of the aspects and embodiments of the present application. The described aspects and embodiments of the application are not limited to the methods and materials described.

As used in this specification and the appended claims, the singular forms "a," "an" and "the" include plural referents unless the content clearly dictates otherwise.

Ranges may be expressed herein as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. It is also understood that when a value is disclosed that "less than or equal to "the value," greater than or equal to the value" and possible ranges between values are also disclosed, as appropriately understood by the skilled artisan. For example, if the value "10" is disclosed the "less than or equal to 10" as well as "greater than or equal to 10" is also disclosed.

The term "pharmaceutically-acceptable excipient" as used herein refers to one or more compatible solid or liquid filler, diluents or encapsulating substances that are suitable for administration into a human. The term "pharmaceutically acceptable carrier" refers to pharmaceutically-acceptable materials, compositions or vehicles, such as liquid or solid fillers, diluents, excipients, solvents or encapsulating materials, involved in carrying or transporting any subject composition or component thereof from one organ, or portion of the body, to another organ, or portion of the body. The term "carrier" denotes an organic or inorganic ingredient, natural or synthetic, with which the active ingredient is combined to facilitate administration. Each excipient or carrier must be "acceptable" in the sense of being compatible with the subject composition and its components and not injurious to the patient. The components of the pharmaceutical compositions also are capable of being co-mingled with the molecules of the present invention, and with each other, in a manner such that there is no interaction that would substantially impair the desired pharmaceutical efficacy.

The term "effective amount" as used herein refers to the amount of a therapy needed to alleviate at least one or more symptoms of the disease or disorder (e.g., inflammation or renal inflammation), and relates to a sufficient amount of pharmacological composition to provide the desired effect. The term "therapeutically effective amount" therefore refers to an amount of a therapy that is sufficient to cause a particular effect when administered to a typical subject. An effective amount as used herein, in various contexts, would also include an amount sufficient to delay the development of a symptom of the disease, alter the course of a symptom of the disease (for example but not limited to, slowing the progression of a symptom of the disease), or reverse a symptom of the disease. Thus, it is not generally practicable to specify an exact "effective amount". However, for any given case, an appropriate "effective amount" can be determined by one of ordinary skill in the art using only routine experimentation.

I. Extrusion Mixture

One aspect of the present application relates to an extrusion mixture for hot melt extrusion. The extrusion mixture comprises (a) the compound shown in formula (I) and

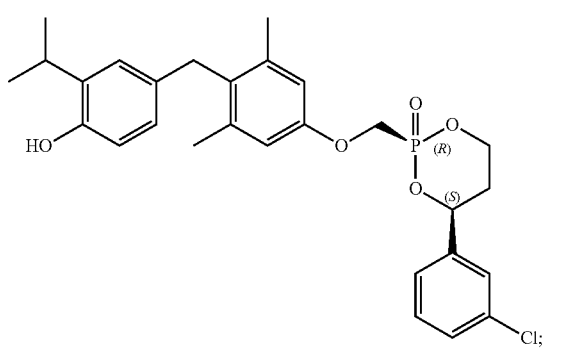

(b) an extrusion medium.

In some embodiment, the compound of formula (I) is in a crystalline form without solvent or crystal water. In some embodiments, the compound of formula (I) is in an amorphous form without solvent or crystal water. In some embodiments, the compound of formula (I) is in the form of a hydrate or solvate.

Examples of the extrusion medium include, but are not limited to, copovidone and hydroxypropyl methylcellulose.

In some embodiments, the extrusion mixture further comprises (c) one or more pharmaceutically acceptable excipients.

During the preparation of the pharmaceutical composition of present application, the extrusion mixture is extruded by hot melt extrusion to form an extruded product. The extruded product is cooled, crushed or cut into particles or powders, optionally mixed with one or more pharmaceutically acceptable carriers, and used for the preparation of the pharmaceutical composition of the present application. In some embodiments, the pharmaceutical composition of the present application is used for the treatment of steatohepatitis.

Extrusion Mixture with Copovidone

In some embodiments, the extrusion mixture comprises, in weight parts, the following components:
(a) 1 part of the compound of formula (I) and (b) 5 to 70 parts of copovidone with a glass transition temperature of 90° C. to 130° C.

In some embodiments, the compound of formula (I) is in a crystalline form without solvent or crystal water. In some embodiments, the compound of formula (I) is in a amorphous form without solvent or crystal water. In some embodiments, the compound of Formula (I) is in the form of a hydrate or solvate.

In some embodiments, the copovidone has a glass transition temperature of 90° C. to 120° C. In some embodiments, the copovidone has a glass transition temperature of 100° C. to 120° C. In some embodiments, the copovidone has a glass transition temperature of 90° C. to 110° C. In some embodiments, the copovidone has a glass transition temperature of 100° C. to 110° C.

In some embodiments, the copovidone is common type or coarse type copovidone. In some embodiments, the copovidone is obtained by copolymerization of 1-vinyl-2-pyrrolidone and vinyl acetate in a mass ratio of 3:2, in which the nitrogen [N] content is 7.0% to 8.0% and the copolymer vinyl acetate ($C_4H_6O_2$) content is 35.3% to 41.4%, calculated on the anhydrous basis. The CAS number of Copovidone is 25086-89-9. Copovidone may have different names according to different naming rules or habits, such as copovidonum, poly (1-vinylpyrrolidone-vinyl acetate), polyvinylpyrrolidone-vinyl acetate copolymer, PVP/VA, PVP/VA copolymer, VP/VA copolymer 60/40, etc. The copovidone can also have different trade names according to the nomenclature of different companies, such as Kollidon® VA64 or Kollidon® VA64 fine (fine powder type) from BASF, Plasdone® S-630 from Ashland, KoVidone® VA64 from BOAI NKY MEDICAL Holdings, and Stardone® VA64 from Star-Tech & JRS Specialty Products.

In some embodiments, the weight ratio of component (a):component (b) in the extrusion mixture is 1:5-70 (i.e., 1 part by weight of component (a) and 5-70 parts by weight of component (b)), 1:5-65, 1:5-60, 1:5-55, 1:5-50, 1:5-45, 1:5-40, 1:5-35, 1:5-30, 1:5-25, 1:5-20, 1:5-15, 1:5-10, 1:10-70, 1:10-65, 1:10-60, 1:10-55, 1:10-50, 1:10-45, 1:10-40, 1:10-35, 1:10-30, 1:10-25, 1:10-20, 1:10-15, 1:15-70, 1:15-65, 1:15-60, 1:15-55, 1:15-50, 1:15-45, 1:15-40, 1:15-35, 1:15-30, 1:15-25, 1:15-20, 1:20-70, 1:20-65, 1:20-60, 1:20-55, 1:20-50, 1:20-45, 1:20-40, 1:20-35, 1:20-30, 1:20-25, 1:25-70, 1:25-65, 1:25-60, 1:25-55, 1:25-50, 1:25-45, 1:25-40, 1:25-35, 1:25-30, 1:30-70, 1:30-65, 1:30-60, 1:30-55, 1:30-50, 1:30-45, 1:30-40, 1:30-35, 1:35-70, 1:35-65, 1:35-60, 1:35-55, 1:35-50, 1:35-45, 1:35-40, 1:40-70, 1:40-65, 1:40-60, 1:40-55, 1:40-50, 1:40-45, 1:45-70, 1:45-65, 1:45-60, 1:45-55, 1:45-50, 1:50-70, 1:50-65, 1:50-60, 1:50-55, 1:55-70, 1:55-65, 1:55-60, 1:60-70, 1:60-65, 1:65-70 or 1:22-33.

In some embodiments, the extrusion mixture further comprises (c) 0.03 to 10 parts of one or more pharmaceutically acceptable excipients. In some embodiments, the one or more pharmaceutically acceptable excipients are selected from the group consisting of non-volatile weak acids, neutral and weakly acidic inorganic substances, and pharmaceutically acceptable excipients with melting point lower than 130° C., 120° C., 110° C., 100° C., 90° C. or 80° C.

Examples of non-volatile weak acids include, but are not limited to, anhydrous citric acid, citric acid monohydrate and mixtures thereof. Examples of neutral and weakly acidic inorganic substances include, but are not limited to, mannitol, lactose monohydrate, lactose anhydrous, sorbitol, calcium hydrogen phosphate anhydrous and colloidal silicon dioxide.

In some embodiments, the one or more pharmaceutically acceptable excipients comprises pharmaceutically acceptable excipients having a melting point below 80° C. In some embodiments, the pharmaceutically acceptable excipients having a melting point below 80° C. are selected from the group consisting of polyethylene glycols such as polyethylene glycol 4000 and polyethylene glycol 6000; lipidic materials such as triethyl citrate, polyethylene glycol succinate; antioxidants such as 2,6-di-tert-butyl-p-cresol and vitamin E; and surfactants such as Poloxamer 188 and Tween 8.

In some embodiments, the one or more pharmaceutically acceptable excipients have a melting point below 80° C. and are selected from the group consisting of anhydrous citric acid and citric acid monohydrate. In some embodiments, the one or more pharmaceutically acceptable excipients are selected from the group consisting of mannitol, lactose monohydrate, lactose anhydrous, sorbitol, calcium hydrogen phosphate anhydrous and colloidal silicon dioxide.

In some embodiments, the weight ratio of components (a):(b):(c) in the extrusion mixture is 1:5-70:0.03-10 (i.e., 1 part by weight of component (a), 5-70 parts by weight of component (b), and 0.03-10 parts by weight of component (c)), 1:5-65:0.03-10, 1:5-60:0.03-10, 1:5-55:0.03-10, 1:5-50:0.03-10, 1:5-45:0.03-10, 1:5-40:0.03-10, 1:5-35:0.03-10, 1:5-30:0.03-10, 1:5-25:0.03-10, 1:5-20:0.03-10, 1:5-15: 0.03-10, 1:5-10:0.03-10, 1:10-70:0.03-10, 1:10-65:0.03-10, 1:10-60:0.03-10, 1:10-55:0.03-10, 1:10-50:0.03-10, 1:10-45:0.03-10, 1:10-40:0.03-10, 1:10-35:0.03-10, 1:10-30: 0.03-10, 1:10-25:0.03-10, 1:10-20:0.03-10, 1:10-15:0.03-10, 1:15-70:0.03-10, 1:15-65:0.03-10, 1:15-60:0.03-10, 1:15-55:0.03-10, 1:15-50:0.03-10, 1:15-45:0.03-10, 1:15-40:0.03-10, 1:15-35:0.03-10, 1:15-30:0.03-10, 1:15-25: 0.03-10, 1:15-20:0.03-10, 1:20-70:0.03-10, 1:20-65:0.03-10, 1:20-60:0.03-10, 1:20-55:0.03-10, 1:20-50:0.03-10, 1:20-45:0.03-10, 1:20-40:0.03-10, 1:20-35:0.03-10, 1:20-30:0.03-10, 1:20-25:0.03-10, 1:25-70:0.03-10, 1:25-65: 0.03-10, 1:25-60:0.03-10, 1:25-55:0.03-10, 1:25-50:0.03-10, 1:25-45:0.03-10, 1:25-40:0.03-10, 1:25-35:0.03-10, 1:25-30:0.03-10, 1:30-70:0.03-10, 1:30-65:0.03-10, 1:30-60:0.03-10, 1:30-55:0.03-10, 1:30-50:0.03-10, 1:30-45: 0.03-10, 1:30-40:0.03-10, 1:30-35:0.03-10, 1:35-70:0.03-10, 1:35-65:0.03-10, 1:35-60:0.03-10, 1:35-55:0.03-10, 1:35-50:0.03-10, 1:35-45:0.03-10, 1:35-40:0.03-10, 1:40-70:0.03-10, 1:40-65:0.03-10, 1:40-60:0.03-10, 1:40-55: 0.03-10, 1:40-50:0.03-10, 1:40-45:0.03-10, 1:45-70:0.03-10, 1:45-65:0.03-10, 1:45-60:0.03-10, 1:45-55:0.03-10, 1:45-50:0.03-10, 1:50-70:0.03-10, 1:50-65:0.03-10, 1:50-

60:0.03-10, 1:50-55:0.03-10, 1:55-70:0.03-10, 1:55-65: 0.03-10, 1:55-60:0.03-10, 1:60-70:0.03-10, 1:60-65:0.03-10, 1:65-70:0.03-10 or 1:22-33:0.03-10.

In some embodiments, the weight ratio of components (a):(b):(c) in the extrusion mixture is 1:5-70:0.1-3, 1:5-65: 0.1-3, 1:5-60:0.1-3, 1:5-55:0.1-3, 1:5-50:0.1-3, 1:5-45:0.1-3, 1:5-40:0.1-3, 1:5-35:0.1-3, 1:5-30:0.1-3, 1:5-25:0.1-3, 1:5-20:0.1-3, 1:5-15:0.1-3, 1:5-10:0.1-3, 1:10-70:0.1-3, 1:10-65:0.1-3, 1:10-60:0.1-3, 1:10-55:0.1-3, 1:10-50:0.1-3, 1:10-45:0.1-3, 1:10-40:0.1-3, 1:10-35:0.1-3, 1:10-30:0.1-3, 1:10-25:0.1-3, 1:10-20:0.1-3, 1:10-15:0.1-3, 1:15-70:0.1-3, 1:15-65:0.1-3, 1:15-60:0.1-3, 1:15-55:0.1-3, 1:15-50:0.1-3, 1:15-45:0.1-3, 1:15-40:0.1-3, 1:15-35:0.1-3, 1:15-30:0.1-3, 1:15-25:0.1-3, 1:15-20:0.1-3, 1:20-70:0.1-3, 1:20-65:0.1-3, 1:20-60:0.1-3, 1:20-55:0.1-3, 1:20-50:0.1-3, 1:20-45:0.1-3, 1:20-40:0.1-3, 1:20-35:0.1-3, 1:20-30:0.1-3, 1:20-25:0.1-3, 1:25-70:0.1-3, 1:25-65:0.1-3, 1:25-60:0.1-3, 1:25-55:0.1-3, 1:25-50:0.1-3, 1:25-45:0.1-3, 1:25-40:0.1-3, 1:25-35:0.1-3, 1:25-30:0.1-3, 1:30-70:0.1-3, 1:30-65:0.1-3, 1:30-60:0.1-3, 1:30-55:0.1-3, 1:30-50:0.1-3, 1:30-45:0.1-3, 1:30-40:0.1-3, 1:30-35:0.1-3, 1:35-70:0.1-3, 1:35-65:0.1-3, 1:35-60:0.1-3, 1:35-55:0.1-3, 1:35-50:0.1-3, 1:35-45:0.1-3, 1:35-40:0.1-3, 1:40-70:0.1-3, 1:40-65:0.1-3, 1:40-60:0.1-3, 1:40-55:0.1-3, 1:40-50:0.1-3, 1:40-45:0.1-3, 1:45-70:0.1-3, 1:45-65:0.1-3, 1:45-60:0.1-3, 1:45-55:0.1-3, 1:45-50:0.1-3, 1:50-70:0.1-3, 1:50-65:0.1-3, 1:50-60:0.1-3, 1:50-55:0.1-3, 1:55-70:0.1-3, 1:55-65:0.1-3, 1:55-60:0.1-3, 1:60-70:0.1-3, 1:60-65:0.1-3, 1:65-70:0.1-3 or 1:22-33:0.1-3.

In some embodiments, the weight ratio of components (a):(b):(c) in the extrusion mixture is 1:5-70:0.2-2, 1:5-65: 0.2-2, 1:5-60:0.2-2, 1:5-55:0.2-2, 1:5-50:0.2:2, 1:5-45:0.2-2, 1:5-40:0.2-2, 1:5-35:0.2-2, 1:5-30:0.2-2, 1:5-25:0.2-2, 1:5-20:0.2-2, 1:5-15:0.2-2, 1:5-10:0.2-2, 1:10-70:0.2-2, 1:10-65: 0.2-2, 1:10-60:0.2-2, 1:10-55:0.2-2, 1:10-50:0.2-2, 1:10-45: 0.2-2, 1:10-40:0.2-2, 1:10-35:0.2-2, 1:10-30:0.2-2, 1:10-25: 0.2-2, 1:10-20:0.2-2, 1:10-15:0.2-2, 1:15-70:0.2-2, 1:15-65: 0.2-2, 1:15-60:0.2-2, 1:15-55:0.2-2, 1:15-50:0.2-2, 1:15-45: 0.2-2, 1:15-40:0.2-2, 1:15-35:0.2-2, 1:15-30:0.2-2, 1:15-25: 0.2-2, 1:15-20:0.2-2, 1:20-70:0.2-2, 1:20-65:0.2-2, 1:20-60: 0.2-2, 1:20-55:0.2-2, 1:20-50:0.2-2, 1:20-45:0.2-2, 1:20-40: 0.2-2, 1:20-35:0.2-2, 1:20-30:0.2-2, 1:20-25:0.2-2, 1:25-70: 0.2-2, 1:25-65:0.2-2, 1:25-60:0.2-2, 1:25-55:0.2-2, 1:25-50: 0.2-2, 1:25-45:0.2-2, 1:25-40:0.2-2, 1:25-35:0.2-2, 1:25-30: 0.2-2, 1:30-70:0.2-2, 1:30-65:0.2-2, 1:30-60:0.2-2, 1:30-55: 0.2-2, 1:30-50:0.2-2, 1:30-45:0.2-2, 1:30-40:0.2-2, 1:30-35: 0.2-2, 1:35-70:0.2-2, 1:35-65:0.2-2, 1:35-60:0.2-2, 1:35-55: 0.2-2, 1:35-50:0.2-2, 1:35-45:0.2-2, 1:35-40:0.2-2, 1:40-70: 0.2-2, 1:40-65:0.2-2, 1:40-60:0.2-2, 1:40-55:0.2-2, 1:40-50: 0.2-2, 1:40-45:0.2-2, 1:45-70:0.2-2, 1:45-65:0.2-2, 1:45-60: 0.2-2, 1:45-55:0.2-2, 1:45-50:0.2-2, 1:50-70:0.2-2, 1:50-65: 0.2-2, 1:50-60:0.2-2, 1:50-55:0.2-2, 1:55-70:0.2-2, 1:55-65: 0.2-2, 1:55-60:0.2-2, 1:60-70:0.2-2, 1:60-65:0.2-2, 1:65-70: 0.2-2 or 1:22-33:0.2-2.

In some embodiments, the extrusion mixture comprises, in weight parts, the following components:

(a) 1 part of the compound of Formula (I);

(b) 15 to 45 parts of copovidone with a glass transition temperature of 100° C. to 120° C.; and (c) 0.1 to 3.0 parts of one or more pharmaceutically acceptable excipients selected from the group consisting of non-volatile weak acids, neutral and weakly acidic inorganic substances, and pharmaceutically acceptable excipients with melting point lower than 80° C.

In some embodiments, the copovidone in (b) has a glass transition temperature of 100° C. to 110° C. In some embodiments, the drug mixture comprises 20 to 40 parts, preferably 20 to 35 parts, more preferably 22 to 33 parts of copovidone.

Extrusion Mixture with Hydroxypropyl Methylcellulose

In some embodiments, the extrusion mixture comprises, in weight parts, the following components:

(a) 1 portion of the compound of Formula (I) and (b) 3 to 40 portions of hydroxypropyl methylcellulose with a glass transition temperature of 90° C. to 130° C.

In some embodiments, the compound of Formula (I) is in a crystalline form without solvent or crystal water. In some embodiments, the compound of Formula (I) is in a amorphous form without solvent or crystal water. In some embodiments, the compound of Formula (I) is in the form of a hydrate or solvate.

In some embodiments, the hydroxypropyl methylcellulose in has a glass transition temperature of 90° C. to 120° C. In some embodiments, the hydroxypropyl methylcellulose has a glass transition temperature of 100° C. to 120° C. In some embodiments, the hydroxypropyl methylcellulose has a glass transition temperature of 90° C. to 110° C. In some embodiments, the hydroxypropyl methylcellulose has a glass transition temperature of 100° C. to 110° C.

In some embodiments, the hydroxypropyl methylcellulose has a CAS number of 9004-65-3. In some embodiments, the hydroxypropyl methylcellulose suitable is the AFFINISOL® by Tao Chemical with a viscosity of 15 cP (HME15LV) or 100 cP viscosity (HME100LV).

In some embodiments, the weight ratio of components (a):(b) in the extrusion mixture is 1:2-40, 1:2-35, 1:2-30, 1:2-25, 1:2-20, 1:2-15, 1:2-10, 1:2-5, 1:6-40, 1:6-35, 1:6-30, 1:6-25, 1:6-20, 1:6-15, 1:6-10, 1:10-40, 1:10-35, 1:10-30, 1:10-25, 1:10-20, 1:10-15, 1:15-40, 1:15-35, 1:15-30, 1:15-25, 1:15-20, 1:20-40, 1:20-35, 1:20-30, 1:20-25, 1:25-40, 1:25-35, 1:25-30, 1:30-40, 1:30-35, 1:35-40, 1:2-25, 1:2-20, 1:2-15, 1:2-10, 1:2-5 or 1:9-15.

In some embodiments, the extrusion mixture further comprises (c) 0.03 to 10 parts of one or more pharmaceutically acceptable excipients.

In some embodiments, the one or more pharmaceutically acceptable excipients in (c) are selected from the group consisting of non-volatile weak acids, neutral and weakly acidic inorganic substances, and pharmaceutically acceptable excipients with melting point lower than 130° C., 120° C., 110° C., 100° C., 90° C. or 80° C. Examples of non-volatile weak acids include, but are not limited to, anhydrous citric acid, citric acid monohydrate and mixtures thereof. Examples of neutral and weakly acidic inorganic substances include, but are not limited to, mannitol, lactose monohydrate, lactose anhydrous, sorbitol, calcium hydrogen phosphate anhydrous and colloidal silicon dioxide.

In some embodiments, the one or more pharmaceutically acceptable excipients have a melting point below 80° C., and are selected from the group consisting of polyethylene glycols such as polyethylene glycol 4000 and polyethylene glycol 6000; lipidic materials such as triethyl citrate, polyethylene glycol succinate; antioxidants such as 2,6-di-tert-butyl-p-cresol andvitamin E; and surfactants such as Poloxamer 188 and Tween 8.

In some embodiments, the one or more pharmaceutically acceptable excipients have a melting point below 80° C. and are selected from the group consisting of anhydrous citric acid and citric acid monohydrate. In some embodiments, the one or more pharmaceutically acceptable excipients are selected from the group consisting of mannitol, lactose monohydrate, lactose anhydrous, sorbitol, calcium hydrogen phosphate anhydrous and colloidal silicon dioxide.

In some embodiments, the weight ratio of components (a):(b):(c) in the extrusion mixture is 1:2-40:0.03-10, 1:2-35:0.03-10, 1:2-30:0.03-10, 1:2-25:0.03-10, 1:2-20:0.03-10, 1:2-15:0.03-10, 1:2-10:0.03-10, 1:2-5:0.03-10, 1:6-40:0.03-10, 1:6-35:0.03-10, 1:6-30:0.03-10, 1:6-25:0.03-10, 1:6-20:0.03-10, 1:6-15:0.03-10, 1:6-10:0.03-10, 1:10-40:0.03-10, 1:10-35:0.03-10, 1:10-30:0.03-10, 1:10-25:0.03-10, 1:10-20:0.03-10, 1:10-15:0.03-10, 1:15-40:0.03-10, 1:15-35:0.03-10, 1:15-30:0.03-10, 1:15-25:0.03-10, 1:15-20:0.03-10, 1:20-40:0.03-10, 1:20-35:0.03-10, 1:20-30:0.03-10, 1:20-25:0.03-10, 1:25-40:0.03-10, 1:25-35:0.03-10, 1:25-30:0.03-10, 1:30-40:0.03-10, 1:30-35:0.03-10, 1:35-40:0.03-10, 1:2-25:0.03-10, 1:2-20:0.03-10, 1:2-15:0.03-10, 1:2-10:0.03-10, 1:2-5:0.03-10 or 1:9-15:0.03-10.

In some embodiments, the weight ratio of components (a):(b):(c) in the extrusion mixture is 1:2-40:0.1-3, 1:2-35:0.1-3, 1:2-30:0.1-3, 1:2-25:0.1-3, 1:2-20:0.1-3, 1:2-15:0.1-3, 1:2-10:0.1-3, 1:2-5:0.1-3, 1:6-40:0.1-3, 1:6-35:0.1-3, 1:6-30:0.1-3, 1:6-25:0.1-3, 1:6-20:0.1-3, 1:6-15:0.1-3, 1:6-10:0.1-3, 1:10-40:0.1-3, 1:10-35:0.1-3, 1:10-30:0.1-3, 1:10-25:0.1-3, 1:10-20:0.1-3, 1:10-15:0.1-3, 1:15-40:0.1-3, 1:15-35:0.1-3, 1:15-30:0.1-3, 1:15-25:0.1-3, 1:15-20:0.1-3, 1:20-40:0.1-3, 1:20-35:0.1-3, 1:20-30:0.1-3, 1:20-25:0.1-3, 1:25-40:0.1-3, 1:25-35:0.1-3, 1:25-30:0.1-3, 1:30-40:0.1-3, 1:30-35:0.1-3, 1:35-40:0.1-3, 1:2-25:0.1-3, 1:2-20:0.1-3, 1:2-15:0.1-3, 1:2-10:0.1-3, 1:2-5:0.1-3 or 1:9-15:0.1-3.

In some embodiments, the weight ratio of components (a):(b):(c) in the extrusion mixture is 1:2-40:0.2-2, 1:2-35:0.2-2, 1:2-30:0.2-2, 1:2-25:0.2-2, 1:2-20:0.2-2, 1:2-15:0.2-2, 1:2-10:0.2-2, 1:2-5:0.2-2, 1:6-40:0.2-2, 1:6-35:0.2-2, 1:6-30:0.2-2, 1:6-25:0.2-2, 1:6-20:0.2-2, 1:6-15:0.2-2, 1:6-10:0.2-2, 1:10-40:0.2-2, 1:10-35:0.2-2, 1:10-30:0.2-2, 1:10-25:0.2-2, 1:10-20:0.2-2, 1:10-15:0.2-2, 1:15-40:0.2-2, 1:15-35:0.2-2, 1:15-30:0.2-2, 1:15-25:0.2-2, 1:15-20:0.2-2, 1:20-40:0.2-2, 1:20-35:0.2-2, 1:20-30:0.2-2, 1:20-25:0.2-2, 1:25-40:0.2-2, 1:25-35:0.2-2, 1:25-30:0.2-2, 1:30-40:0.2-2, 1:30-35:0.2-2, 1:35-40:0.2-2, 1:2-25:0.2-2, 1:2-20:0.2-2, 1:2-15:0.2-2, 1:2-10:0.2-2, 1:2-5:0.2-2 or 1:9-15:0.2-2.

In some embodiments, the extrusion mixture comprises, in weight parts, the following components:

(a) 1 part of the compound of Formula (I);

(b) 6 to 20 parts of hydroxypropyl methylcellulose with a glass transition temperature of 100° C. to 120° C.; and (c) 0.1 to 3.0 parts of one or more pharmaceutically acceptable excipients selected from the group consisting of non-volatile weak acids, neutral inorganic substances, weakly acidic inorganic substances, and other pharmaceutically acceptable excipients with a melting point below 80° C.

In some embodiments, the compound of Formula (I) is in a crystalline form without solvent or crystal water. In some embodiments, the compound of Formula (I) is in a amorphous form without solvent or crystal water. In some embodiments, the compound of Formula (I) is in the form of a hydrate or solvate. In some embodiments, the extrusion mixture comprises 9 to 15 parts of (b). In some embodiments, the extrusion mixture comprises 0.2-2 parts of (c). In some embodiments, the non-volatile weak acids in (c) are selected from the group consisting of anhydrous citric acid, citric acid monohydrate and mixtures thereof. In some embodiments, the one or more pharmaceutically acceptable excipients are selected from the group consisting of mannitol, lactose monohydrate, lactose anhydrous, sorbitol, calcium hydrogen phosphate anhydrous and colloidal silicon dioxide. In some embodiments, the other pharmaceutically acceptable excipients with a melting point below 80° C. are selected from the group consisting of polyethylene glycols such as polyethylene glycol 4000 and/or polyethylene glycol 6000; lipidic materials such as triethyl citrate, polyethylene glycol succinate; antioxidants such as 2,6-di-tert-butyl-p-cresol and vitamin E; and surfactants such as Poloxamer 188 and Tween 8.

II. Pharmaceutical Composition

Another aspect of the present application relates to a pharmaceutical composition comprising an extruded product of the extrusion mixture of the present application and one or more pharmaceutically acceptable carriers. In some embodiments, the pharmaceutical composition may be used for the treatment of steatohepatitis and conditions related to steatohepatitis.

In some embodiments, the pharmaceutical composition comprises an extruded product made from the extrusion mixture of the present application. In some embodiments, the extruded product is in the form of particles or powders. In some embodiments, the pharmaceutical application further comprises one or more pharmaceutically acceptable carriers.

Examples of the pharmaceutically acceptable carriers include, but are not limited to, calcium carbonate, calcium phosphate, silica dioxide, sugars, starches, cellulose derivatives, gelatin, sodium stearyl fumarate, polymers such as polyethylene glycols, water, saline, phosphate buffered saline, dextrose, glycerol, ethanol, polyalcohols such as mannitol, sorbitol, and sodium chloride.

In some embodiments, the pharmaceutical composition comprises the extruded product and the one or more pharmaceutical carriers at an extruded product:pharmaceutical carrier weight ratio in the range of 1:0.1 to 1:10, 1:0.1 to 1:6, 1:0.1 to 1:3, 1:0.1 to 1:1, 1:0.1 to 1:0.6, 1:0.1 to 1:0.3, 1:0.3 to 1:10, 1:0.3 to 1:6, 1:0.3 to 1:3, 1:0.3 to 1:1, 1:0.3 to 1:0.6, 1:1 to 1:10, 1:1 to 1:6, 1:1 to 1:3, 1:3 to 1:10, 1:3 to 1:6, or 1:6 to 1:10.

In some embodiments, the pharmaceutical composition further comprises wetting or emulsifying agents, preservatives or buffering reagents, which enhance the shelf life or effectiveness of the therapeutic agents.

In some embodiments, the pharmaceutical composition is formulated for oral administration. In some embodiments, the pharmaceutical composition is formulated as a tablet, a capsule, a granule or a dry suspension. In some embodiments, the pharmaceutical composition is formulated as a tablet or a capsule. In some embodiments, the pharmaceutical composition is formulated as a hydroxypropyl cellulose capsule.

III. Methods of Preparation

Another aspect of the present application relates to a method for preparing the extrusion product of the present application. The method comprises the step of extruding the extrusion mixture of the present application by hot melt extrusion at an extrusion die or extrusion outlet temperature (the hot melt extrusion temperature) of 80° C. to 135° C. to produce an extrusion product. In some embodiments, the hot melt extrusion temperature is between 100° C. and 130° C. In some embodiments, the hot melt extrusion temperature is between 80° C. and 130° C., 80° C. and 120° C., 80° C. and 110° C., 80° C. and 100° C., 80° C. and 90° C., 90° C. and 130° C., 90° C. and 120° C., 90° C. and 110° C., 90° C. and 100° C., 100° C. and 130° C., 100° C. and 120° C., 100° C. and 110° C., 110° C. and 130° C., 110° C. and 120° C., or 120° C. and 130° C.

In some embodiments, the extruding step is performed with a twin-screw hot melt extrusion device. In some embodiments, the twin-screw hot melt extrusion device has a screw diameter between 8 mm and 50 mm and an extrusion speed between 10 rpm and 300 rpm.

In some embodiments, the hot melt extrusion is performed with a residence time (i.e., the period between the time the extrusion mixture enters the hot melt extrusion device and the time the extrusion mixture extruded at the die) of less than 30 min, 25 min, 20 min, 15 min or 10 min. In some embodiments, the hot melt extrusion is performed with a residence time 15 min.

In some embodiments, the method further comprises the step of cooling the extruded product. In some embodiments, the method further comprises the step of breaking, crushing, grinding or cutting the extruded product into granules, particle or powders. In some embodiments, the method further comprises the step of sieving and drying the granules, particle or powders of the extruded product.

In some embodiments, the hot melt extruded product, after cooling, is crushed or cut into particles or powders. The resulting granules or powder can be directly filled into capsules to make capsules, or can be packaged into granules to make granules. The resulting granules or powders may also be mixed with other pharmaceutically acceptable carrier and further processed into tablets, capsules, granules, or dry suspensions.

Another aspect of the present application relates to a method for preparing the pharmaceutical composition of the present application. The method comprises the steps of processing the extruded product of the present application into tablets or capsules. In some embodiments, the processing step comprises the substeps of mixing the granules, particles or powder of the extruded product with one or more pharmaceutically acceptable carrier, and processing the resulting mixture into tablets, capsules, granules or dry mixes, preferably tablets or capsules.

In some embodiments, the pharmaceutical composition of the present application is processed into tablets or filled into capsules. In some embodiments, the pharmaceutical composition of the present application is filled into hydroxypropyl methylcellulose capsules.

In accordance with a specific embodiment of the present application, the preparation method of a pharmaceutical composition of the application includes the following steps:

1. Pretreatment of active pharmaceutical ingredient (API) and excipients: The API and excipients to be used for formulation study should be crushed, sieved and dried by conventional means of preparation technology to remove the lumps during storage and reduce the moisture content of easily hygroscopic excipients, so that they meet the standards for further preparation;

2. Compounding: Weigh the API and excipients for hot melt extrusion according to the formulation ratio and preparation scale;

3. Mixing: mix the API and excipients completed in compounding by conventional means of preparation technology to form an extrusion mixture;

4. Hot melt extrusion: Set the extrusion temperature for different areas of the extruder, respectively; after preheating to the set temperature, keep the temperature for 15 min 30 min, evenly add the extrusion mixture by manual feeding or weightlessness automatic feeder feeding, extrude at the preset extrusion speed; by adjusting the temperature, screw speed and feeding speed in different areas of the extruder barrel, control the extrusion die temperature between 100° C. and 130° C., keep the screw torque within a stable range, and the extruded product (extrudate) is transparent; adjust the extrusion speed and feeding speed, so that the retention time of the material in the hot melt extruder barrel is controlled within 30 min.

5. Crushing of extrudate: The cooled extrudate is crushed by conventional means of preparation technology;

6. General mixing: According to the prescription ratio, add other carrier/excipients, and mix the above materials by conventional mixing means to form a pharmaceutical mixture;

7. Preparation: Process the pharmaceutical mixture into tablets or capsules according to the proportion of each prescription;

8. Packaging: Package the tablets or capsules with a suitable method;

9. Storage: Store the packaged drug tablets or capsules, which contain the compound of formula (I) at room temperature (not exceeding 30° C.).

IV. Methods of Treatment

Another aspect of the present application relates to a method for treating steatohepatitis or a steatohepatitis related condition in a subject. The method comprises the step of administering to a subject in need of such treatment, an effective amount of the pharmaceutical composition of the present application. In some embodiments, the pharmaceutical composition of the present application is administered orally. In some embodiments, the pharmaceutical composition of the present application is administered orally in a tablet or capsule form. In some embodiments, the pharmaceutical composition of the present application is administered twice a day, daily or every other day.

Examples of steatohepatitis related conditions include, but are not limited to, steatosis, hepatocellular ballooning, fibrosis, and sclerosis.

After repeated experimental studies, the inventor unexpectedly found that the pharmaceutical composition of the present application can not only greatly improve the in vitro solubility of the compound of formula (I), but also meet the needs of long-term room temperature storage of the thermally unstable compounds of formula (I).

The advantages of the pharmaceutical composition of the present application are:

(1) The pharmaceutical composition of the present application can greatly improve the dissolution rate of the compound of formula (I), and achieve the supersaturation maintenance time similar to the existing technology;

(2) The pharmaceutical composition of the present application can be stored at room temperature (not exceeding 30° C.) for a long time without refrigeration.

The present application is further illustrated by the following examples that should not be construed as limiting. The contents of all references, patents, and published patent applications cited throughout this application, as well as the Figures and Tables, are incorporated herein by reference.

EXAMPLES

Example 1

Formulation Composition:

TABLE 1

Formulation composition for Example 1

| Composition Formulation (mg) | Formulation Number | | | | | |
|---|---|---|---|---|---|---|
| | A1 | B1 | C1 | D1 | E1 | F1 |
| Formula (I) compound | 5 | 1 | 1 | 5 | 5 | 10 |
| Copovidone Kollidon VA64 | 0 | 45 | 40 | 0 | 165 | 0 |
| Copovidone Plasdone S-630 | 75 | 0 | 0 | 110 | 0 | 200 |
| Polyethylene glycol 6000 | 0 | 3 | 1 | 4 | 3.5 | 0 |
| Anhydrous Citric Acid | 0 | 0 | 0 | 0 | 1.5 | 0 |
| Colloidal silka dioxide | 0 | 1 | 0 | 1 | 0 | 0 |
| Extrudate Weight | 80 | 50 | 42 | 120 | 175 | 210 |
| Excipients | A1 | B1 | C1 | D1 | E1 | F1 |
| Calcium phosphate dibasic | 60 | 0 | 12 | 42 | 42 | 72 |
| Mannitol | 136 | 39 | 35 | 116 | 116 | 379 |
| Colloidal silca dioxide | 1.5 | 0.5 | 0.4 | 1.5 | 1 | 5 |
| Sodium Stearyl Fumarate | 2.5 | 0.5 | 0.6 | 2.5 | 3 | 4 |
| Total amount of excipients | 200 | 40 | 48 | 162 | 162 | 460 |
| Amounts | 280 | 90 | 90 | 282 | 337 | 670 |

Process:

1. Pretreatment of API and excipients: The API and excipients to be used for formulation study should be crushed, sieved and dried by conventional means of preparation technology to remove the lumps during storage and reduce the moisture content of easily hygroscopic excipients, so that they meet the standards for further preparation;

2. Compounding: Weigh the API and excipients for hot melt extrusion according to the formulation ratio and preparation scale;

3. Mixing: mix the API and excipients completly in compounding by conventional means of preparation technology;

4. Hot melt extrusion: Set the extrusion temperature for different areas of the extruder, respectively; After preheating to the set temperature, keep the temperature for 15 min~30 min, evenly add the mixed API and excipients by manual feeding or weightlessness automatic feeder feeding, extrude at the preset extrusion speed; By adjusting the temperature, screw speed and feeding speed in different areas of the extruder barrel, control the extrusion die temperature between 100° C. and 130° C., keep the screw torque within a stable range, and the extruded material is transparent; Adjust the extrusion speed and feeding speed, so that the retention time of the material in the hot melt extruder barrel is controlled within 30 min;

5. Crushing of extrudate: The cooled extrudate is crushed by conventional means of preparation technology;

6. Total mixing: According to the formulation ratio, add additional excipients, and mix the above materials by the conventional mixing means of preparation technology;

7. Preparation: Compress the prescriptions A1, D1 and E1 into 13 mm×6 mm (length×width) capsule-shaped tablets, and control the hardness of the tablets at 70 N~130 N. Formula F1 was compressed into 17.2 mm×8.1 mm (length×width) capsule-shaped tablets, and the hardness of the tablets was controlled between 90 N and 160 N. Fill the total blend of formulations B1 and C1 into Vcaps Plus No. 4 hydroxypropyl cellulose capsules;

8. Packaging: Fill the tablets of formulations A1, D1, E1 and F1 and the capsules of formulations B1 and C1 into high-density ethylene bottles, and seal with aluminum film;

9. Storage: Store the tablets or capsules of the compound shown in formula (I) in packaged bottles at room temperature (not exceeding 30° C.).

Example 2

Composition of Formulation:

TABLE 2

Composition of Example 2 Formulation

| Composition (mg) | Formulation No. | | | | | |
|---|---|---|---|---|---|---|
| | G1 | H1 | I1 | J1 | K1 | L1 |
| Compound of formula (I) | 5 | 5 | 5 | 5 | 5 | 5 |
| Copovidone Kollidon VA64 | 165 | 82.5 | 165 | 150 | 82.5 | 82.5 |
| Polyethylene glycol 6000 | 5 | 2.5 | 0 | 0 | 0 | 0 |
| Poloxamer 188 | 0 | 0 | 5 | 20 | 5 | 0 |
| Vitamin E polyethylene glycol succinate (TPGS) | 0 | 0 | 0 | 0 | 0 | 5 |
| Weight of extrudate | 175 | 90 | 42 | 175 | 92.5 | 92.5 |

Preparation Process:

1. Pretreatment of API and excipient materials: the API and excipient materials to be used in formulation research are crushed, sieved and dried by the conventional methods of preparation technology to remove caking during storage and reduce water content of hygroscopic excipient materials so as to meet the standards for further preparation;

2. Compounding: API and excipient materials for hot melt extrusion are weighed according to formulation proportion and preparation scale;

3. Mixing: API and excipient were mixed uniformly by conventional methods of preparation technology;

4. Hot melt extrusion: Setting the extrusion temperature for different areas of the extruder. After preheating to the set temperature, keep the temperature for 15 min-30 min, Add the uniformly mixed API and excipient by manual feeding or weight loss automatic feeder feeding uniformly, and extrude at preset extrusion speed. By adjusting the temperature of different areas of extruder barrel, screw rotation speed and feeding speed, the temperature of the extrusion die is controlled between 100° C. and 130° C., the screw torque is kept in a stable range, and the extruded material is transparent. Adjust the extrusion speed and feeding speed to control the residence time of materials in the barrel of hot melt extruder within 30 min;

5. Crushing the extrudate: Crushing the cooled extrudate by conventional means of preparation technology and passing through a 40-mesh sieve; process Comparative Example 1

Prepared according to the a2 formulation in Table 2 and following preparation

TABLE 3

Formulation composition for Comparative Example 1

| Composition Formulation (mg) | a2 |
|---|---|
| Granulation | / |
| Formula (I) compound | 5 |
| beta-cyclodextrin | 99 |

TABLE 3-continued

Formulation composition for Comparative Example 1

| Composition Formulation (mg) | a2 |
|---|---|
| Anhydrous Citric Acid | 0.5 |
| Colloidal silka dioxide | 0.5 |
| Total Wet Granulation | 105 |
| Excipients | / |
| Calcium phosphate dibasic | 45 |
| mannitol | 126 |
| Colloidal silca dioxide | 1.5 |
| Sodium Stearyl Fumarate | 2.5 |
| Total amount of excipients | 175 |
| Amounts | 280 |

Preparation Process:

1. Pretreatment of API and excipients: The API and excipients to be used for formulation study should be crushed, sieved and dried by conventional means of preparation technology to remove the lumps during storage and reduce the moisture content of easily hygroscopic excipients, so that they meet the standards for further preparation;

2. Compounding: API and excipients for granulation by wet method according to formulation ratio and preparation scale;

3. Mixing: mix the API and excipients completed in compounding by conventional means of preparation technology;

4. Wet granulation: Use water as binder, evenly add it into the mixed granulation API and excipients, pass through a 24-mesh stainless steel screen for granulation, take the wet granules after granulation and dry them in a blast oven at 65° C. until the moisture content is less than 3% (rapid moisture determination by infrared weight loss at 105° C.).

5. Granulation: Granulate the dried granules by passing them through a 24-mesh stainless steel screen;

6. General mixing: According to the formulation ratio, add other excipients, and mix the above materials by conventional mixing means of preparation technology;

7. Preparation: compress the total mixed granules into 13 mm-6 mm (length*width) capsule tablets, and control the hardness of the tablets at 70 N~130 N;

8. Packaging: put the tablets of Formulation a2 into a high-density ethylene bottle and seal with aluminum film;

9. Storage: Store the tablets of the compound shown in formula (I) in packaged bottles at room temperature (not exceeding 30° C.)

Comparative Example 2

Formulation Composition:

TABLE 4

Formulation composition for Comparative Example 2

| Composition Formulation (mg) | Formulation Number | |
|---|---|---|
| | b2 | c2 |
| Formula (I) compound | 5 | 5 |
| Polyethylene caprolactam-polyvinyl acetate-polyethylene glycol copolymer Soluplus | 110 | 0 |
| Copovidone Kollidon VA64 | 0 | 55 |
| Polyethylene Glycol 6000 | 0 | 1.5 |
| Anhydrous citric acid | 0.5 | 0.5 |
| Colloidal silicon dioxide | 0.5 | 0 |
| Extrudate | 116 | 62 |

TABLE 4-continued

Formulation composition for Comparative Example 2

| Composition Formulation (mg) | Formulation Number | |
|---|---|---|
| | b2 | c2 |
| Excipients | b2 | c2 |
| Anhydrous calcium hydrogen phosphate | 24 | 0 |
| Mannitol | 136 | 29 |
| Colloidal silicon dioxide | 1.5 | 0.5 |
| Sodium Stearyl Fumarate | 2.5 | 0.5 |
| Total amount of excipients | 164 | 30 |
| Total Amounts | 280 | 92 |

Preparation Process:

1. Pretreatment of API and excipients: The API and excipients to be used for formulation study should be crushed, sieved and dried by conventional means of preparation technology to remove the lumps during storage and reduce the moisture content of easily hygroscopic excipients, so that they meet the standards for further preparation;

2. Compounding: API and excipients for granulation by wet method according to formulation ratio and preparation scale;

3. Mixing: Mix the API and excipients completed in the compounding by conventional means of preparation technology;

4. hot melt extrusion: Set the extrusion temperature according to different areas of the extruder; After preheating to the set temperature, keep the temperature for 15 min~30 min, evenly add the mixed API and excipients in the form of manual feeding or weightlessness automatic feeder feeding, extrude at the preset extrusion speed; by adjusting the temperature, screw speed and feeding speed in different areas of the extruder cylinder, control the extrusion die temperature between 100° C. and 130° C., keep the screw torque within a stable range, and the material is transparent after extrusion; Adjust the extrusion speed and feeding speed, so that the retention time of the material in the hot melt extruder barrel is controlled within 30 min;

5. Crushing of extrudate: The cooled extrudate is crushed by conventional means of preparation technology;

6. Total mixing: According to the formulation ratio, add additional excipients, and mix the above materials by the conventional mixing means of preparation technology;

7. Preparation: The formulation b2 was compressed into 13 mm-6 mm (length*width) capsule tablets, and the hardness of the tablets was controlled at 70 N~130 N; the total mixture of formulation c2 was filled into VcapsPlus type 4 hydroxypropyl cellulose capsules..

8. Packaging: Fill the tablets of formulations b2 and the capsules of formulations c2 into high-density ethylene bottles, and seal with aluminum film;

9. Storage: Store the compounds shown in formula (I) tablets or capsules packaged in bottle at room temperature (not exceeding 30° C.)

Comparative Example 3

It is prepared according to the E1 formulation (as shown in Table 5 below) in Example 1 of Chinese Invention Patent Application 202010105909.9 and the following preparation process.

TABLE 5

| Formulation composition for Comparative Example 3 | |
|---|---|
| Composition Formulation (mg) | d2 |
| Formula (I) compound | 5 |
| Polyethylene Glycol 1000 | 300 |
| Polyethylene Glycol 6000 | 100 |
| Poloxamer 188 | 90 |
| Anhydrous Citric Acid | 5 |
| Content Weight | 500 |
| Type of filled gelatin capsule | NO. 1 |

Preparation Process:

1. Preparation of blank matrix: At 65° C., polyethylene glycol 1000, polyethylene glycol 4000, polyethylene glycol 6000, poloxamer 188, and anhydrous citric acid were successively added and stirred to completely melt;

2. De-bubbling: Standing to completely eliminate bubbles;

3. Addition of compounds shown in formula (I): Add the drug substance of compounds shown in formula (I) under stirring, and continue stirring to completely melt it into the matrix;

4. Filling capsule: Transfer the prepared molten contents to the preheated insulated cylinder of the capsule filling machine, enable the stirring function, fill the molten contents into the gelatin hard capsule with the preset filling parameters (control the average filling volume difference ≤2.5%, single capsule filling volume difference ≤5.0%), and cover the capsule cap;

5. Cooling: Lay flat at room temperature to quickly cool and solidify the contents;

6. Packaging: The capsule is loaded into a high-density ethylene bottle and sealed with aluminum film;

7. Storage: Store the formula (I) compound capsules packaged bottled at 2~8° C.

Comparative Example 4

Prepared according to e2 and f2 formulations in Table 6 and the following preparation process.

TABLE 6

| Formulation Composition of Comparative Example 4 | | |
|---|---|---|
| | Formulation No. | |
| Formulation Composition (mg) | e2 | f2 |
| Compound of formula (I) | 5.0 | 5.0 |
| Copovidone Kollidon VA64 | 62.7 | 41.25 |
| Polyethylene glycol 6000 | 1.9 | 1.25 |
| Weight of extrudate | 69.6 | 47.5 |

Preparation Process:

1. Pretreatment of API and excipient: the API and excipient to be used in formulation research are crushed, sieved and dried by the conventional means of preparation technology to remove caking during storage and reduce water content of hygroscopic excipient so as to meet the standards for further preparation;

2. Compounding: API and excipient for hot melt extrusion are weighed according to formulation proportion and preparation scale;

3. Mixing: the API and excipient were mixed uniformly by conventional means of preparation technology;

4. Hot melt extrusion: setting the extrusion temperature for different areas of the extruder; After preheating to the set temperature, keep the temperature for 15 min-30 min., add the uniformly mixed API and excipient in the way of manual feeding or weight loss automatic feeder feeding uniformly, and extrude at preset extrusion speed; By adjusting the temperature of different areas of the extruder barrel, screw rotation speed and feeding speed, the temperature of the extrusion die is controlled between 100° C. and 130° C., the screw torque is kept in a stable range, and the extruded material is transparent; Adjust the extrusion speed and feeding speed to control the residence time of materials in barrel of hot melt extruder within 30 min;

5. Crushing the extrudate: Crushing the cooled extrudate by conventional means of preparation technology and passing through a 40-mesh sieve;

Comparative Example 5

Prepared according to g2 prescription in table 7 and the following preparation process.

TABLE 7

| Formulation composition of Comparative Example 4 | |
|---|---|
| Composition formulation (mg) | g2 |
| Compound represented by formula (I) | 5 |
| Copovidone Kollidon VA64 | 165 |
| Mannitol | 150 |
| Total | 320 |

Preparation Process:

1. Pretreatment of API and excipient: API and excipient to be used in formulation research are crushed, sieved and dried by the conventional means of preparation technology to remove caking during storage and reduce the moisture content of hygroscopic excipient so as to meet the standards for further preparation;

2. Compounding: weighing API and excipient for dry granulation according to formulation proportion and preparation scale;

3. Mixing: mixing the API and excipient with finished ingredients evenly by the conventional means of preparation technology;

4. Dry granulation: roll the evenly mixed API and excipient under the pressure of 5.0 MPa and make them into thin slices.

5. Grading: grading by sieving with 24 mesh stainless steel sieve;

6. Packaging: packaging the granules obtained from Formulation e2 into double aluminum strips according to the dosage and sealing;

7. Preservation: the packaged tablets of the compound shown in formula (I) are stored at room temperature (not exceeding 30° C.).

Effect Example 1

Take the granules obtained by grinding after thermal melting extrusion according to the formulations A1~F1 of Example 1, grind the granules after wet granulation and drying according to the a2 formulation of contrast Example 1, grind the granules obtained by grinding after thermal melting extrusion according to the b2, and c2 formulations of Comparative Example 2, and prepare the capsules according to the d2 formulation of Comparative Example 3, and compare the dissolution curves in water for 6 samples each.

Dissolution conditions: Take 900 mL of degassed water at 37° C.±0.5° C. as the dissolution medium, and perform 50 rpm for paddle method. The granules are directly and precisely weighed and then put in, and the capsules prepared according to the d2 formulation of Comparative Example 3 are put in the sedimentation basket for input. Take samples at 10, 20, 30, 45, 60, 90 and 120 min, respectively. Take the subsequent filtrate and dilute it with an equal proportion of 75% acetonitrile aqueous solution. Determine the concentration of the compound as shown in formula (I) by HPLC. Calculate the cumulative dissolution percentage of the compound as shown in formula (I) at different time points.

HPLC assay conditions: Select a chromatographic column packed with octadecylsilane bonded silica gel (Welch Ultimate ® XB-C18 4.6*150 mm, 5 μm, or equivalent chromatographic column) and 0.05% trifluoroacetic acid aqueous solution-acetonitrile (30:70) as mobile phase, flow rate 1.0 ml/min, column temperature 30° C., detection wavelength 230 nm. Accurately inject 20 μl of the reference solution and the test solution (50 μl of the 1 mg B1 and C1 formulation and 10 μl of the 10 mg F1 formulation) into the column respectively, record the chromatograms, and calculate the dissolution of each capsule with respect to the peak area by the external standard method.

Figure 2:
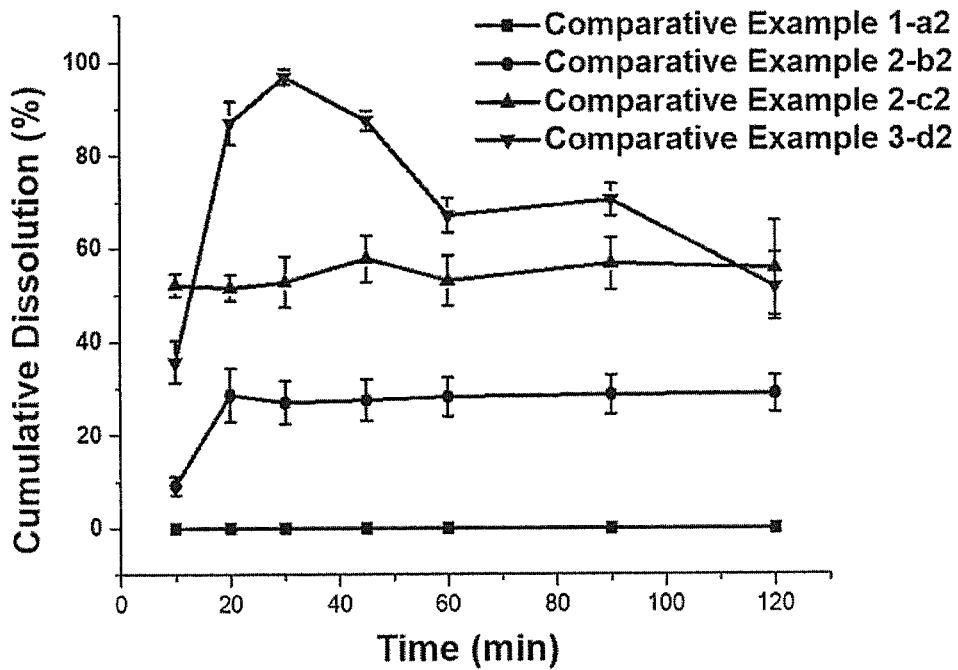
FIG. 2 is the dissolution curve (Effect Example 1) of the compositions prepared according to a2-d2 formulation in Comparative Examples 1-3 in water (n=6).

Results:

I. As shown in Table 8 and FIG. 1, with the formulation at the proportion of each embodiment of the present invention, the compounds shown in formula (I) can achieve the results of maximum dissolution >85%, which is similar to the results of the semisolid capsule of the Chinese invention patent application 202010105909.9 (compare the results of the d2 formulation of Comparative Example 3 in Table 9 and FIG. 2).

II. β-cyclodextrin is a common solubilizing excipient, and the dissolution of poorly soluble drugs can usually be improved to a certain extent after granulation with its wet method. However, the experimental results using the a2 formulation in example 1 showed that the solubility of the compounds shown in formula (I) was less than 1% at a higher proportion (1:19.8) of β-cyclodextrin dosage. This indicates that random application of common solubilization means does not necessarily improve the dissolution of the compounds shown in formula (I).

III. In the b2 formulation of Comparative Example 2, the polyethylene caprolactam—polyvinyl acetate—polyethylene glycol graft copolymer Soluplus, a popular hot melt extrusion excipient for solubilization, was mixed with the compound shown in formula (I) in a ratio of 22:1 and hot melt extrusion was performed, and the results showed a solubility of less than 1%. This suggests that the random selection of a hot melt extrusion excipient for solubilization does not necessarily have the effect of solubilizing the compounds shown in formula (I).

IV. In the b2 formulation of Comparative Example 2, the hot melt extrusion of copovidone Kollidon VA64 and the compound shown in formula (I) in a ratio of 1:11 had a maximum solubility of 57.9% within 2 hours, which was less than 85%. It can be seen that the proportion required for different excipients to achieve solubilization is also different.

Conclusion:

Simple application solubilization methods, such as β-cyclodextrin solubilization, are not suitable for increasing the dissolution of compounds shown in formula (I); simple application hot melt extrusion technology without screening materials, such as polyethylene caprolactam-polyvinyl acetate-polyethylene glycol copolymer Soluplus is not suitable for increasing the dissolution of compounds shown in formula (I); simple selection of high ratio excipients, such as copovidone Kollidon VA64 with the ratio of compounds shown in Formula (I) of 1:11, is not ideal. Therefore, only by selecting specific solubilizing materials and maintaining a reasonable ratio, can the compounds shown in formula (I) be satisfactorily solubilized.

TABLE 8

Aqueous Dissolution Results of Formulation Samples from Example 1 (n = 6)

| Time | Dissolution Rate (Mean ± SD, %) | | | | | |
|---|---|---|---|---|---|---|
| min | A1 | B1 | C1 | D1 | E1 | F1 |
| 10 | 79.1 ± 6.6 | 41.9 ± 5.6 | 68.0 ± 8.8 | 92.3 ± 1.9 | 98.8 ± 2.1 | 70.0 ± 14.7 |
| 20 | 87.2 ± 2.3 | 81.8 ± 10.2 | 73.6 ± 10.5 | 84.1 ± 3.9 | 98.1 ± 1.8 | 78.7 ± 7.1 |
| 30 | 89.5 ± 2.0 | 87.0 ± 1.7 | 85.6 ± 13.7 | 82.8 ± 4.6 | 95.6 ± 4.5 | 84.7 ± 2.7 |
| 45 | 79.0 ± 6.2 | 86.1 ± 6.8 | 83.6 ± 17.3 | 84.0 ± 8.7 | 97.6 ± 1.9 | 86.9 ± 4.5 |
| 60 | 77.0 ± 4.5 | 80.2 ± 15.8 | 68.2 ± 16.2 | 83.5 ± 4.1 | 102.6 ± 9.4 | 87.5 ± 5.1 |
| 90 | 76.9 ± 10.6 | 65.9 ± 13.4 | 54.2 ± 15.1 | 80.1 ± 4.0 | 98.1 ± 2.8 | 86.8 ± 7.2 |
| 120 | 75.8 ± 11.6 | 57.6 ± 8.4 | 46.7 ± 22.7 | 84.1 ± 2.4 | 96.3 ± 2.6 | 84.5 ± 5.5 |

TABLE 9

Aqueous Dissolution Results of Formulation Samples from Comparative Examples

| Time | Dissolution Rate (Mean ± SD, %) | | | |
|---|---|---|---|---|
| min | a2 | b2 | c2 | d2 |
| 10 | <1.0 | 9.2 ± 2.0 | 52.2 ± 2.5 | 1.6 ± 0.4 |
| 20 | <1.0 | 28.6 ± 5.8 | 51.6 ± 2.8 | 2.6 ± 0.3 |
| 30 | <1.0 | 27.0 ± 4.6 | 52.9 ± 5.5 | 3.4 ± 0.8 |
| 45 | <1.0 | 27.5 ± 4.4 | 57.9 ± 4.9 | 3.9 ± 0.8 |
| 60 | <1.0 | 28.2 ± 4.1 | 53.2 ± 5.4 | 2.6 ± 0.6 |
| 90 | <1.0 | 28.7 ± 4.2 | 56.9 ± 5.5 | 4.8 ± 0.9 |
| 120 | <1.0 | 28.9 ± 3.9 | 55.9 ± 10.2 | 5.0 ± 0.6 |

Effect Example 2

The pH of digestive juice in human gastrointestinal tract is increasing. Maintaining a high degree of supersaturation after oral administration is the prerequisite for insoluble drugs to be absorbed into systemic circulation to exert their efficacy. In this example, a simple dissolution test design in vitro (dissolution test of 2h+4h) was used to explain the reasons for choosing the composition ratio and preparation process of the present invention.

Take the granules obtained by hot melt extrusion according to G1-L1 formulation of Example 2, the granules obtained by hot melt extrusion according to g2-f2 formulation of Comparative Example 4, and the granules obtained by dry granulation according to g2 formulation of Comparative Example 5, and investigate the pH transition and supersaturation maintenance time of simulated human digestive juice.

The dissolution conditions were as follows: firstly, 750 mL degassed hydrochloric acid solution with pH 2.0 at 37° C.±0.5° C. was used as dissolution medium, and the dissolution was carried out with stirring at 50 rpm by paddle method for 2 hours, then degassed 250 mL 200 mM pH 6.8 phosphate buffer solution was added, and the dissolution was continued with stirring at 50 rpm by paddle method for 4 hours. Particles are directly and accurately weighed and then put in, and samples are taken at 15, 30, 45, 60, 90, 120, 180, 210, 240 and 360 min after putting in, and the subsequent filtrate is diluted with 75% acetonitrile water solution in equal proportion, and the concentration of the compound shown in formula (I) is determined by HPLC, and the formula (I) is calculated at different time points The HPLC determination conditions were the same as those in Effect Example 1.

Figure 3:
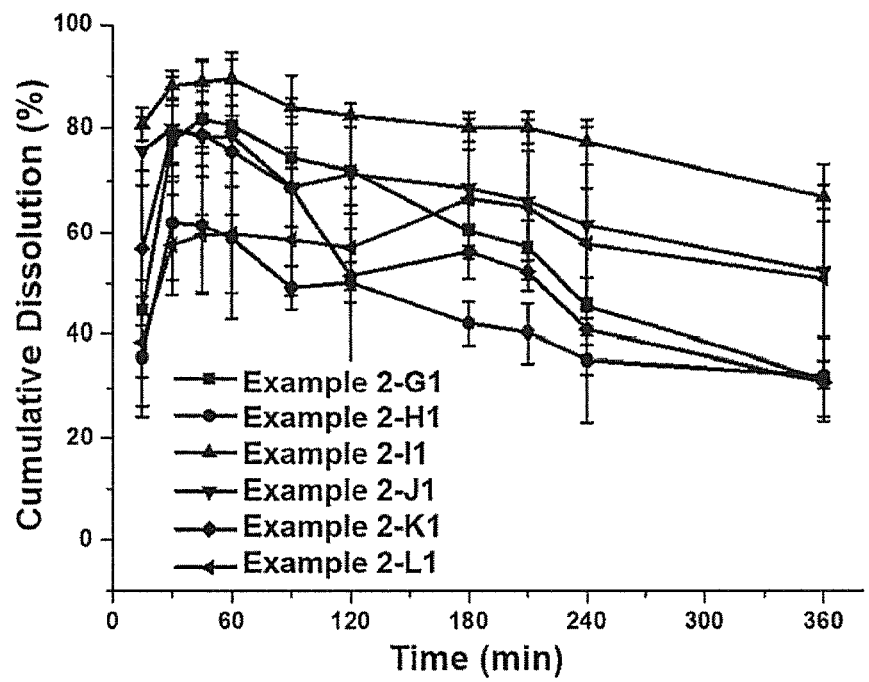
FIG. 3 is the dissolution curve (Effect Example 2) of compositions prepared according to G1-L1 formulation in Example 2 (n=6)
Figure 4:
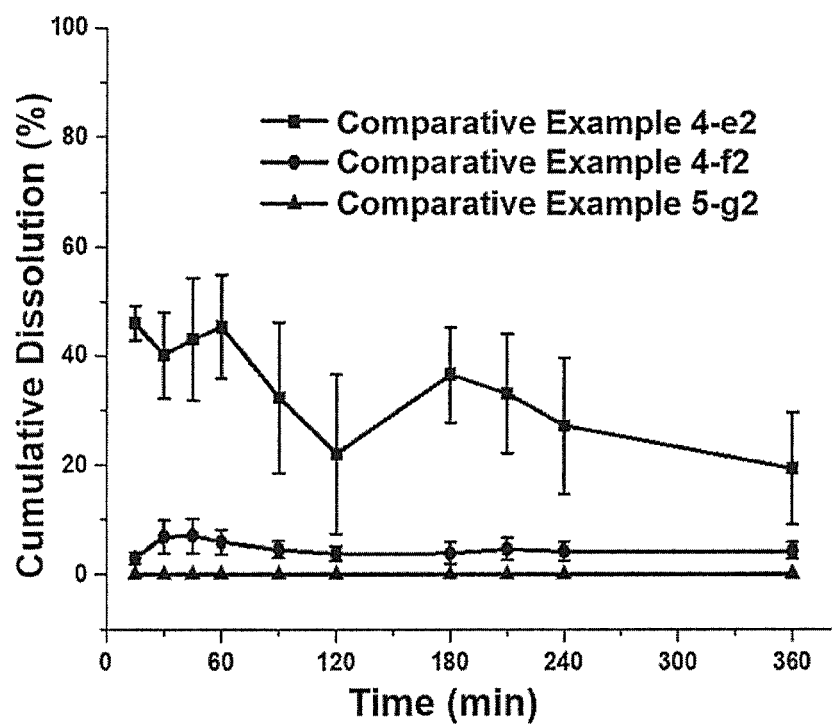
FIG. 4 is the dissolution curve (Effect Example 2) of compositions prepared according to e2-g2 formulation in Comparative Examples 4-5 (n=6).

Results:

I. As shown in Table 10 and FIG. 3, the compound shown in formula (I) can achieve the highest dissolution rate of >60% and maintain dissolution rate of >30% at 6 h.

II. When the proportion of copovidone is reduced to less than 15 parts, such as e2 and f2 in Comparative Example 4, when the proportion of copovidone is reduced to 12.54 parts and 8.25 parts respectively, the highest dissolution rate is only 46.1% and 7.1%, and the dissolution rate at 6 h is only 19.4% and 4.4%. This indicates that the ratio of copovidone is directly related to solubilization effect, and when the dosage is less than 15 parts, it is difficult to maintain supersaturated concentration at a higher degree.

III. In the g2 formulation of Comparative Example 5, the amount of copovidone is 33 parts, but because the dry granulation process is used instead of the hot melt extrusion, the results show that the dissolution within 6 hours is less than 1%. This indicates that the solubilization effect of the compound shown in formula (I) can be achieved only after hot melt extrusion, and the preparation process is very important for the implementation effect of the composition.

Conclusion:

The results of Example 2 show once again that only by adopting a specific proportion of Copovidone and a specific hot melt extrusion preparation process can higher dissolution and longer supersaturation maintenance time be achieved.

TABLE 11

Dissolution results of formulation samples in Comparative Examples 4-5 (n = 6)

| Time | Dissolution (Mean ± SD,%) | | |
|---|---|---|---|
| Min | e2 | f2 | g2 |
| 15 | 46.1 ± 3.2 | 3.1 ± 1.1 | <1.0 |
| 30 | 40.1 ± 7.9 | 6.9 ± 3.0 | <1.0 |
| 45 | 43.1 ± 11.3 | 7.1 ± 3.1 | <1.0 |
| 60 | 45.4 ± 9.6 | 6.0 ± 2.2 | <1.0 |
| 90 | 32.4 ± 13.9 | 4.6 ± 1.5 | <1.0 |
| 120 | 22.0 ± 14.6 | 3.9 ± 1.3 | <1.0 |
| 180 | 36.6 ± 8.8 | 4.0 ± 2.0 | <1.0 |
| 210 | 33.2 ± 11.0 | 4.7 ± 2.0 | <1.0 |
| 240 | 27.2 ± 12.4 | 4.3 ± 1.7 | <1.0 |
| 360 | 19.4 ± 10.3 | 4.4 ± 1.5 | <1.0 |

Effect Example 3

Take capsules prepared according to the B1 formulation of Example 1 and tablets prepared according to the E1 formulation, respectively place them in high-density polyethylene bottles, seal with aluminum film, and then place them at 30° C.±2° C. with 65%±5% relative humidity for accelerated test. Take the capsules prepared according to the formulation d2 of Comparative Example 3, place them in a high-density polyethylene bottle, seal with aluminum film, and then place them at 25° C.±2° C. with relative humidity of 60%±10% for acceleration test. Related substances were determined for Group B1 capsules, Group E1 tablets and Group d2 capsules at the accelerated 1-month time point.

Determination of related substances: Using a column packed with octadecylsilane bonded silica gel (ACE Ultra-Core 2.5 SuperC18 (4.6*150 mm) or equivalent) and 10 mM potassium dihydrogen phosphate aqueous solution as mobile phase A and acetonitrile as mobile phase B, perform gradient elution according to Table 12 (volume ratio); flow rate: 1.0 mL/min, detection wavelength: 278 nm, column temperature: 45° C.

TABLE 12

| Time (min) | mobile phase A (%) | mobile phase B (%) |
|---|---|---|
| 0.00 | 80 | 20 |
| 0.50 | 80 | 20 |
| 8.00 | 45 | 55 |
| 15.00 | 45 | 55 |
| 25.00 | 30 | 70 |

TABLE 10

Dissolution results of formulation samples in Effect Example 2 (n = 6)

| Time | Dissolution (Mean ± SD, %) | | | | | |
|---|---|---|---|---|---|---|
| Min | G1 | H1 | I1 | J1 | K1 | L1 |
| 15 | 44.7 ± 12.4 | 35.8 ± 11.5 | 80.7 ± 3.1 | 75.7 ± 6.5 | 56.8 ± 15.2 | 38.5 ± 12.1 |
| 30 | 77.6 ± 6.7 | 62.0 ± 11.4 | 88.1 ± 2.9 | 79.9 ± 9.9 | 79.4 ± 6.3 | 57.5 ± 9.8 |
| 45 | 81.7 ± 5.3 | 61.5 ± 13.7 | 88.8 ± 4.4 | 78.2 ± 14.6 | 78.8 ± 6.0 | 59.5 ± 11.3 |
| 60 | 80.5 ± 5.7 | 58.9 ± 16.7 | 89.4 ± 5.2 | 78.4 ± 14.8 | 75.6 ± 6.7 | 59.8 ± 11.8 |
| 90 | 74.4 ± 6.4 | 49.1 ± 4.3 | 83.9 ± 1.7 | 68.8 ± 21.3 | 68.7 ± 7.5 | 58.6 ± 13.8 |
| 120 | 72.0 ± 8.2 | 50.1 ± 4.0 | 82.4 ± 2.2 | 71.3 ± 10.5 | 51.5 ± 17.3 | 57.0 ± 8.4 |
| 180 | 60.3 ± 5.5 | 42.0 ± 4.2 | 80.1 ± 2.8 | 68.6 ± 13.1 | 56.2 ± 5.4 | 66.6 ± 9.3 |
| 210 | 57.2 ± 5.2 | 40.3 ± 5.6 | 80.0 ± 3.0 | 66.1 ± 15.5 | 52.2 ± 3.8 | 65.0 ± 10.6 |
| 240 | 45.3 ± 5.7 | 35.3 ± 2.6 | 77.3 ± 4.3 | 61.5 ± 18.6 | 40.8 ± 17.8 | 57.7 ± 10.9 |
| 360 | 31.8 ± 7.6 | 32.5 ± 2.6 | 66.9 ± 2.3 | 52.2 ± 20.9 | 31.2 ± 7.9 | 50.8 ± 11.4 |

TABLE 12-continued

| Time (min) | mobile phase A (%) | mobile phase B (%) |
|---|---|---|
| 50.00 | 15 | 85 |
| 50.10 | 80 | 20 |
| 55.00 | 80 | 20 |

Take an appropriate amount of compounds and impurity reference substances as shown in formula (I), add acetonitrile to dissolve and dilute to produce a solution containing 0.5 mg of compounds and 0.001 mg of impurities per ml, as the system suitability test solution. Accurately inject 50 µl into the liquid chromatograph, and record the chromatogram. The resolution between the known impurities and the adjacent peaks should not be less than 1.5. Take 10 capsules, accurately weighed, pour the contents into a 100 ml volumetric flask, wash the inner wall of the capsule with acetonitrile for several times, and combine the washing liquid into the volumetric flask (for tablets, take 10 tablets, accurately weighed, grind into fine powder, accurately weigh an appropriate amount of tablet powder), dissolve with acetonitrile and prepare a solution containing 0.5 mg of the compound shown in formula (I) per ml as the solution; accurately measure 50 µl of the test solution, inject into the liquid chromatograph, and record the chromatogram. Calculate the sum of impurities and all impurities in compound capsules (or tablets) as shown in formula (I) by peak area normalization method.

Results:

I. As shown in Table 13, for Example 1, the capsules and tablets prepared according to the formulations B1 and E1 were subjected to accelerated investigation at 30° C.±2° C. and 65%±5% relative humidity for 1 month, and the determination results of related substances showed that no significant change was found in all known individual impurities, unknown individual impurities and total impurities of the compounds shown in formula (I), especially the sum of GLC02-Z6 and GLC02-Z7 only increased by 0.02% and 0.04%, respectively. For the production batch, as shown in Table 14, for Example 1, the capsules and tablets prepared according to the formulations B1 and E1 were subjected to accelerated investigation at 30° C.±2° C. and 65%±5% relative humidity for 6 month, and the determination results of related substances showed that no significant change was found in all known individual impurities, unknown individual impurities and total impurities of the compounds shown in formula (I).

II. As shown in Table 13, for Comparative Example 3, after the capsules prepared according to d2 formulation were subjected to accelerated stability study at 25° C.±2° C. and 60%±10% relative humidity for 1 month, the determination results of related substances showed that the sum of GLC02-Z6 and GLC02-Z7 increased by 1.32%, the total impurities increased by 1.14%, and the related substances changed significantly. For the production batch, as shown in Table 14, for Comparative Example 3, after the capsules prepared according to d2 formulation were subjected to accelerated stability study at 25° C.±2° C. and 60%±10% relative humidity for 3 month, the determination results of related substances showed that the sum of GLC02-Z6 and GLC02-Z7 increased by 2.69%, the total impurities increased by 2.0%, and the related substances changed significantly.

TABLE 13

Effect of accelerated stability conditions on related substances in drug product

| | Related Substances (%) | | | | | |
|---|---|---|---|---|---|---|
| | Example 1 B1 Formulation Capsules | | Example 1 E1 Formulation Tablet | | Comparative Example 3 d2 Formulation Capsules | |
| Impurities | 0 month | Accelerated 1 month | 0 month | Accelerated 1 month | 0 month | Accelerated 1 month |
| ASC41-SM1 | Not detected | Not detected | Not detected | Not detected | 0.04 | 0.04 |
| ASC41-SM2 | Not detected | 0.02 | Not detected | 0.02 | Not detected | Not detected |
| ASC41-A | 0.16 | 0.15 | 0.18 | 0.18 | 0.06 | 0.06 |
| GLC02-Z2 | Not detected | Not detected | 0.04 | 0.03 | 0.02 | 0.08 |
| GLC02-Z3 | 0.03 | 0.02 | 0.03 | Not detected | 0.08 | Not detected |
| GLC02-Z4 | Not detected | Not detected | Not detected | Not detected | Not detected | Not detected |
| GLC02-Z11 | 0.03 | 0.03 | 0.03 | 0.03 | 0.06 | 0.05 |
| Sum of GLC02-Z6 and GLC02-Z7 | 0.07 | 0.09 | 0.10 | 0.14 | 0.08 | 1.40 |
| Largest Single unknown impurity | 0.21 | 0.21 | 0.21 | 0.24 | 0.10 | 0.14 |
| Total impurities | 1.00 | 1.02 | 1.30 | 1.34 | 0.66 | 1.80 |

TABLE 14

Effect of different accelerated stability study on related substances in formulation for production batch

| | Related substances (%) | | | | |
|---|---|---|---|---|---|
| | Example 1 B1 formulation capsule (production batch) | | | | |
| Impurity name | 0 month | Accelerate 1 months | Accelerate 2 months | Accelerate 3 months | Accelerate 6 months |
| ASC41-SM1 | Not detected | Not detected | Not detected | Not detected | Not detected |
| ASC41-SM2 | Not detected | Not detected | Not detected | Not detected | Not detected |
| ASC41-A | 0.15% | 0.22% | 0.16% | 0.08% | 0.13% |
| GLC02-Z2 | 0.08% | 0.09% | 0.08% | 0.07% | 0.08% |
| GLC02-Z3 | Not detected | Not detected | Not detected | Not detected | Not detected |
| GLC02-Z4 | Not detected | Not detected | Not detected | Not detected | Not detected |
| GLC02-Z11 | 0.04% | 0.05% | 0.02% | 0.03% | 0.04% |

TABLE 14-continued

Effect of different accelerated stability study on related substances in formulation for production batch

| Sum of GLC02-Z6 and GLC02-Z7 | Not detected | Not detected | 0.05% | 0.04% | Not detected |
|---|---|---|---|---|---|
| Other largest single unknown impurity | 0.02% | Not detected | 0.02% | 0.04% | 0.06% |
| Total impurities | 0.28% | 0.35% | 0.32% | 0.29% | 0.32% |

Related substances (%)

Example 1
E1 formulation tablets (production batch)

| Impurity name | 0 month | Accelerate 1 months | Accelerate 2 months | Accelerate 3 months | Accelerate 6 months |
|---|---|---|---|---|---|
| ASC41-SM1 | Not detected | Not detected | Not detected | Not detected | Not detected |
| ASC41-SM2 | Not detected | Not detected | Not detected | Not detected | Not detected |
| ASC41-A | 0.15% | 0.21% | 0.16% | 0.07% | 0.13% |
| GLC02-Z2 | 0.08% | 0.08% | 0.08% | 0.07% | 0.09% |
| GLC02-Z3 | Not detected | Not detected | Not detected | Not detected | Not detected |
| GLC02-Z4 | Not detected | Not detected | Not detected | Not detected | Not detected |
| GLC02-Z11 | 0.01% | 0.02% | 0.02% | 0.01% | 0.02% |
| Sum of GLC02-Z6 and GLC02-Z7 | Not detected | Not detected | 0.04% | 0.03% | Not detected |
| Other largest single unknown impurity | 0.01% | Not detected | 0.02% | 0.03% | 0.07% |
| Total impurities | 0.26% | 0.32% | 0.32% | 0.21% | 0.31% |

Related substances (%)

Comparative Example 3
d2 Formulation Capsule (production batch)

| Impurity name | 0 month | Accelerate 0.5 months | Accelerate 1 months | Accelerate 1.5 months | Accelerate 3 months |
|---|---|---|---|---|---|
| ASC41-SM1 | 0.06% | 0.06% | 0.06% | 0.06% | 0.06% |
| ASC41-SM2 | Not detected | Not detected | Not detected | Not detected | Not detected |
| ASC41-A | 0.02% | 0.02% | 0.03% | 0.03% | 0.02% |
| GLC02-Z2 | Not detected | 0.03% | 0.05% | 0.07% | 0.14% |
| GLC02-Z3 | 1.10% | 0.21% | 0.03% | Not detected | Not detected |
| GLC02-Z4 | Not detected | Not detected | Not detected | Not detected | Not detected |
| GLC02-Z11 | 0.03% | 0.05% | 0.07% | 0.07% | 0.08% |
| Sum of GLC02-Z6 and GLC02-Z7 | 0.11% | 0.52% | 0.95% | 1.40% | 2.80% |
| Other largest single unknown impurity | 0.05% | 0.05% | 0.05% | 0.05% | 0.10% |
| Total impurities | 1.70% | 1.20% | 1.50% | 2.10% | 3.70% |

Conclusion:

The accelerated results showed that the capsules or tablets of the compounds shown in formula (I) prepared according to the formulation of Example 1 had good results after accelerated stability study for 6 month at a temperature of 30° C.±2° C. and a relative humidity of 65%±5%, indicating that it has the prospect of long-term storage at room temperature.

The preliminary accelerated stability study results for 3 months under the conditions of temperature 25° C.±2° C. and relative humidity 60% 10% showed that the semi-solid capsule of the compound shown in formula (I) prepared according to the formulation of Comparative Example 3, the related substances, especially the sum of GLC02-Z6 and GLC02-Z7 changed significantly, which indicated that the formulation was only suitable for long-term use at 2° C.~8° C., not suitable for long term storage at room temperature.

While various embodiments have been described above, it should be understood that such disclosures have been presented by way of example only and are not limiting. Thus, the breadth and scope of the subject compositions and methods should not be limited by any of the above-described exemplary embodiments, but should be defined only in accordance with the following claims and their equivalents.

The above description is for the purpose of teaching the person of ordinary skill in the art how to practice the present invention, and it is not intended to detail all those obvious modifications and variations of it which will become apparent to the skilled worker upon reading the description. It is intended, however, that all such obvious modifications and variations be included within the scope of the present invention, which is defined by the following claims. The claims are intended to cover the components and steps in any sequence which is effective to meet the objectives there intended, unless the context specifically indicates the contrary.

What is claimed is:

1. A pharmaceutical composition, comprising the following components in weight portions:
(a) 1 part of the compound of formula (I)

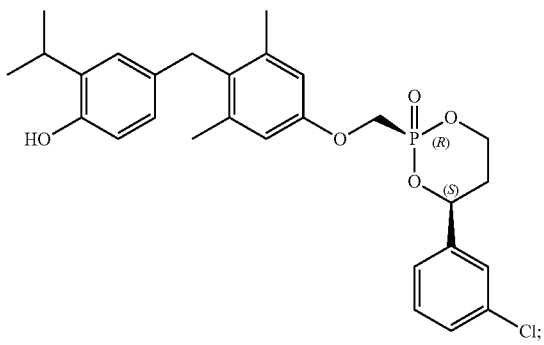

(I)

and
(b) 15 to 45 parts of copovidone with a glass transition temperature of 90° C. to 130° C.,
wherein the composition is obtained by mixing components (a) and (b), followed by hot melt extrusion.

2. The pharmaceutical composition of claim 1, wherein components (a) and (b) are mixed and undergo hot melt extrusion at a temperature in the range of 80° C.-135° C.

3. The pharmaceutical composition of claim 1, comprising 20 to 40 parts of copovidone.

4. The pharmaceutical composition of claim 1, comprising 22 to 33 pans of copovidone.

5. The pharmaceutical composition of claim 1, further comprising:
(c) 0.1 to 3.0 parts of one or more pharmaceutically acceptable excipients selected from the group consisting of non-volatile weak acids, neutral or weakly acidic inorganic substances, and pharmaceutically acceptable excipients with melting point lower than 80° C.,
wherein the composition is obtained by mixing components (a), (b) and (c), followed by hot melt extrusion at a temperature in the range of 80° C.-135° C.

6. The pharmaceutical composition of claim 5, wherein the one or more pharmaceutically acceptable excipients comprise anhydrous citric acid, citric acid monohydrate, or a mixture thereof.

7. The pharmaceutical composition of claim 5, wherein the one or more pharmaceutically acceptable excipients comprise one or more neutral or weakly acidic inorganic substances selected from the group consisting of mannitol, lactose monohydrate, lactose anhydrous, sorbitol, calcium hydrogen phosphate anhydrous and colloidal silicon dioxide.

8. The pharmaceutical composition of claim 5, wherein the one or more pharmaceutically acceptable excipients comprise one or more excipients selected from one or more of the group c polyethylene glycol, polyethylene glycol 4000, polyethylene glycol 6000; lipidic materials, triethyl citrate, vitamin E, polyethylene glycol succinate; antioxidants, 2,6-di-tert-butyl-p-cresol, surfactants, Poloxamer 188 and Tween 80.

9. The pharmaceutical composition of claim 1, wherein the pharmaceutical composition is formulated in a tablet or capsule form.

10. A method for preparing the pharmaceutical composition of claim 1, comprising the steps of:
extruding a mixture of components (a) and (b) by hot melt extrusion at hot melt extrusion temperature is between 80° C. and 135° C. to form an extrusion product;
cooling the extrusion product; and
breaking the cooled extrusion product into granules, particles or powders by cutting, crushing or grinding.

11. The method of claim 10, further comprising the step of:
processing the granules, particles or powders obtained in the breaking step into tablets, capsules.

12. The method of claim 10, wherein the mixture of components (a) and (b) is extruded with a twin screw hot melt extrusion device; wherein the screw diameter of the twin screw hot melt extrusion is between 8 mm and 50 mm, and the extrusion speed is between 10 rpm and 300 rpm, wherein retention time of the hot melt extrusion is less than 30 min.

13. A method of treating steatohepatitis, comprising the step of:
administering to a subject in need of such treatment an effective amount of the pharmaceutical composition of claim 1.

* * * * *